United States Patent
Muhlenberg et al.

(10) Patent No.: US 7,321,798 B2
(45) Date of Patent: Jan. 22, 2008

(54) TRANS-SEPTAL/TRANS-MYOCARDIAL VENTRICULAR PACING LEAD

(75) Inventors: Lambert Muhlenberg, Landgraaf (NL); Chester L. Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 235 days.

(21) Appl. No.: 11/096,510

(22) Filed: Mar. 31, 2005

(65) Prior Publication Data

US 2006/0224224 A1    Oct. 5, 2006

(51) Int. Cl.
*A61N 1/05* (2006.01)

(52) U.S. Cl. ....................... 607/126; 606/151

(58) Field of Classification Search ................ 607/116, 607/119, 122, 123, 126, 128–133, 137; 606/151, 606/157; 600/374, 375
See application file for complete search history.

(56) References Cited

U.S. PATENT DOCUMENTS

| | | | |
|---|---|---|---|
| 4,946,457 A * | 8/1990 | Elliott | 606/1 |
| 5,144,949 A | 9/1992 | Olson | |
| 5,158,078 A | 10/1992 | Bennett et al. | |
| 5,293,869 A * | 3/1994 | Edwards et al. | 600/375 |
| 5,300,107 A * | 4/1994 | Stokes et al. | 607/126 |
| 5,312,453 A | 5/1994 | Shelton et al. | |
| 5,336,252 A | 8/1994 | Cohen et al. | |
| 5,451,235 A | 9/1995 | Lock et al. | |
| 5,662,698 A * | 9/1997 | Altman et al. | 607/123 |
| 5,709,707 A | 1/1998 | Lock et al. | |
| 5,728,140 A | 3/1998 | Salo et al. | |
| 5,741,297 A * | 4/1998 | Simon | 606/213 |
| 6,048,553 A | 4/2000 | Beckett | |
| 6,245,012 B1 | 6/2001 | Kleshinski | |
| 6,440,152 B1 | 8/2002 | Gainor et al. | |
| 6,551,344 B2 * | 4/2003 | Thill | 606/213 |
| 6,746,404 B2 | 6/2004 | Schwartz | |
| 7,082,335 B2 | 7/2006 | Klein et al. | |
| 7,212,869 B2 * | 5/2007 | Wahlstrom et al. | 607/126 |
| 2002/0198563 A1 | 12/2002 | Gainor et al. | |
| 2003/0032998 A1 | 2/2003 | Altman | |
| 2003/0045901 A1 | 3/2003 | Opolski | |
| 2003/0139819 A1 | 7/2003 | Beer et al. | |
| 2003/0144694 A1 | 7/2003 | Chanduszko et al. | |
| 2003/0181945 A1 | 9/2003 | Opolski et al. | |
| 2003/0195530 A1 | 10/2003 | Thill | |
| 2003/0199962 A1 | 10/2003 | Struble et al. | |
| 2003/0204233 A1 | 10/2003 | Laske et al. | |
| 2003/0225421 A1 | 12/2003 | Peavey et al. | |
| 2003/0229386 A1 | 12/2003 | Rosenman et al. | |

(Continued)

FOREIGN PATENT DOCUMENTS

EP    0596625    5/1994

*Primary Examiner*—Kristen D. Mullen
*Assistant Examiner*—Eugene T Wu
(74) *Attorney, Agent, or Firm*—Michael C. Soldner; Paul H. McDowall

(57) ABSTRACT

An medical electrical lead in embodiments of the teachings may include one or more of the following features: (a) a lead body having a proximal end and a distal end, (b) a conductor traversing from the proximal end to the distal end, (c) an electrode disposed at the distal end of the lead body and electrically coupled to the conductor adapted to electrically stimulate a heart, (d) occlusion fabric disposed at the distal end of the lead body and supported by the electrode in a shape adapted to cover holes in the heart, and (f) a second electrode adapted to provide bipolar electrical stimulation of the heart.

15 Claims, 13 Drawing Sheets

U.S. PATENT DOCUMENTS

| | | |
|---|---|---|
| 2004/0073242 A1 | 4/2004 | Chanduszko |
| 2004/0087968 A1 | 5/2004 | Core |
| 2004/0092973 A1 | 5/2004 | Chanduszko et al. |
| 2004/0093017 A1 | 5/2004 | Chanduszko |
| 2004/0098121 A1 | 5/2004 | Opolski |
| 2004/0127855 A1 | 7/2004 | Core |
| 2004/0133236 A1 | 7/2004 | Chanduszko |
| 2004/0176788 A1 | 9/2004 | Opolski |
| 2004/0176797 A1 | 9/2004 | Opolski |
| 2004/0176799 A1 | 9/2004 | Chanduszko et al. |
| 2004/0230283 A1 | 11/2004 | Prinzen et al. |
| 2005/0065589 A1 | 3/2005 | Schneider et al. |
| 2005/0085883 A1 | 4/2005 | Ollivier et al. |

* cited by examiner

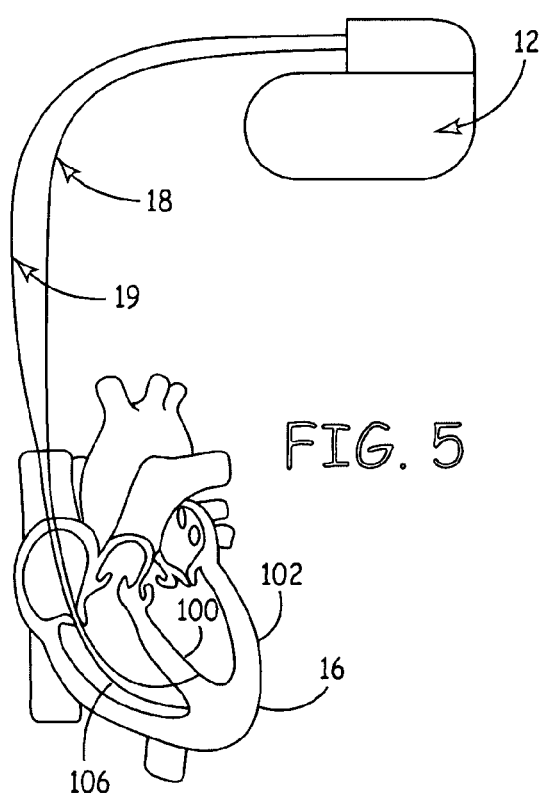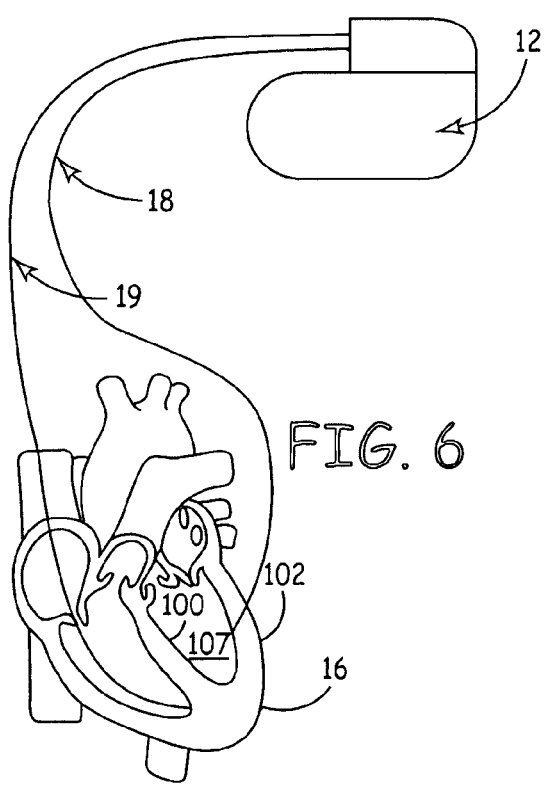
FIG. 5 trans-septal approach
FIG. 6 trans-myocardial approach unipolar configuration bipolar configuration

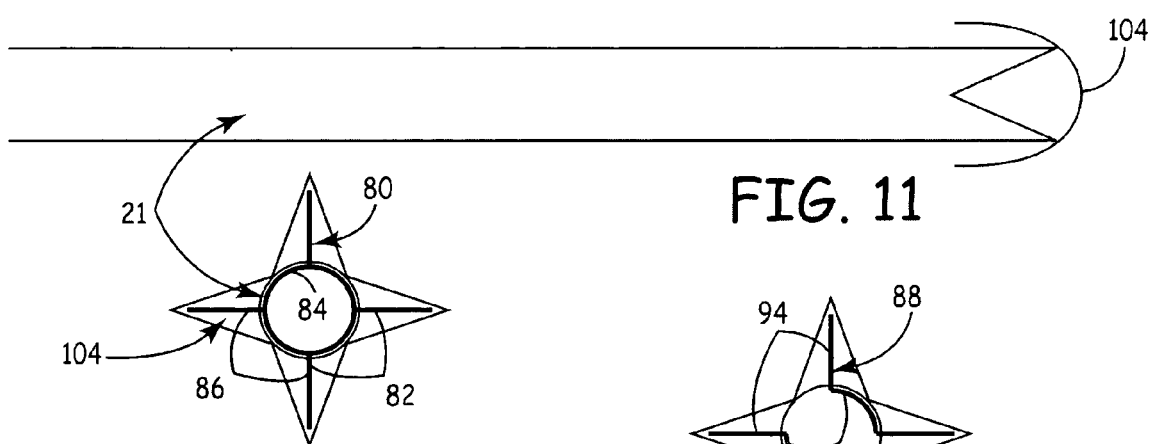
FIG. 11
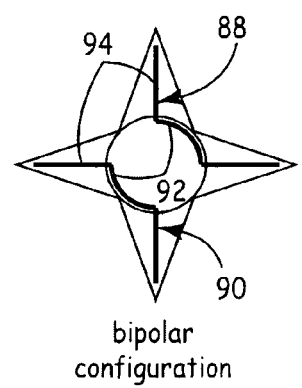
unipolar configuration
FIG. 12
bipolar configuration
FIG. 13

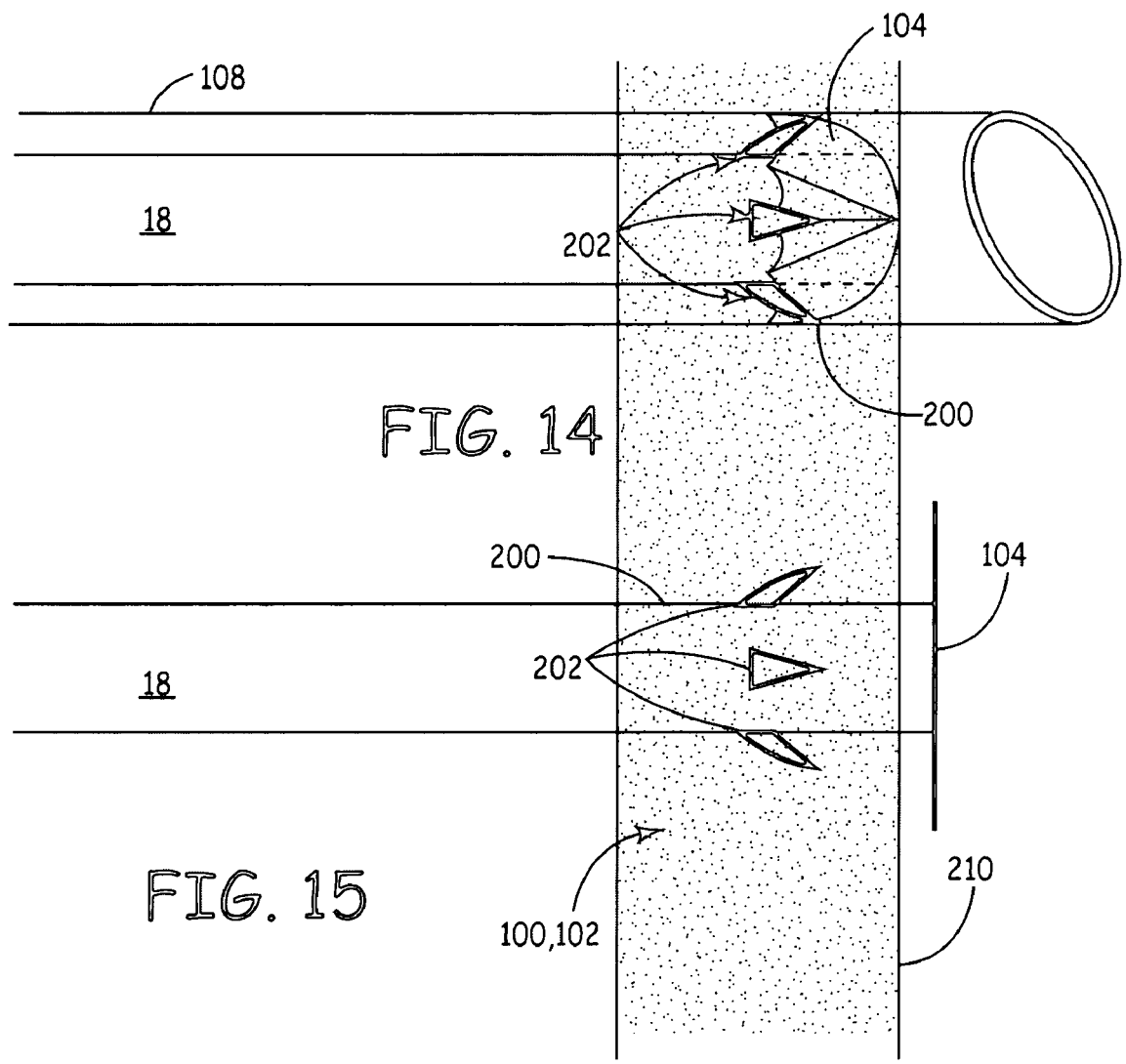

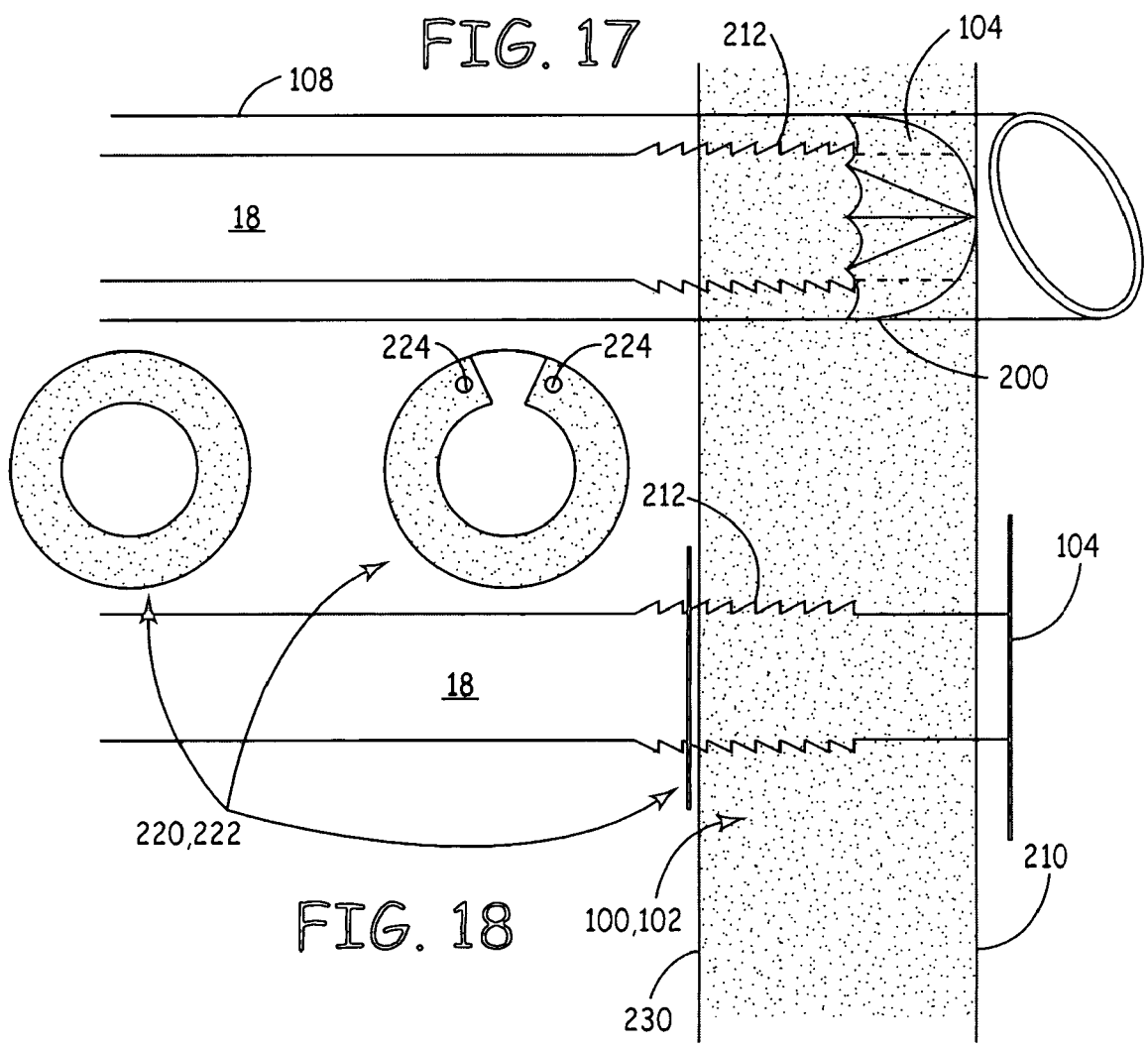

TRANS-SEPTAL/TRANS-MYOCARDIAL VENTRICULAR PACING LEAD

FIELD

The present teachings relates to methods and an implantable apparatus for treating cardiac arrhythmia, particularly ventricular fibrillation. More particularly, the present teachings relate to methods and an implantable apparatus for cardiac resynchronization therapy to heart failure patients.

BACKGROUND

Various types of pacing leads have been developed for endocardial implant, typically in the right ventricle (RV) or right atrial appendage, as well as the coronary sinus. These flexible leads usually are constructed having an outer polymeric sheath encasing one or more electrical conductors. One conductor is typically attached at its distal tip to the shank portion of a tip electrode. In bipolar or multipolar leads, one or more further conductors are provided in coaxial or co-linear relation to the first conductor and is connected at its distal end to a more proximally located, ring-shaped electrodes situated along the lead body. The proximal ends of each conductor are coupled to a connector, which includes a single pin in unipolar leads, and additional pins or in-line rings in bipolar and multipolar leads.

Stimulation in both single chamber and dual chamber pacemakers with ventricular stimulation normally takes place in the apex of the RV. A conventional pacemaker of this type typically requires two electrodes. One of these electrodes is placed in the right atrium (RA) and the other in the apex of the RV. The electrodes sense electrical activity in the heart and to provide stimulation pulses as needed to rectify arrhythmias.

Further, while stimulation in the apex has proved clinically effective, there is a need to limit RV pacing to more closely simulate the natural cardiac system.

In a healthy heart, electrical potential originates in the sinoatrial (SA) node, travels to the atrioventricular (AV) node, and finally to the myocardial mass through the Purkinge fibers. This provides a sequential activation of the atria and the ventricles. Specifically, the sequential polarization and depolarization of the atria and the ventricle results in a naturally synchronized sinus rhythm.

There is increasing evidence that the sequence of electrical activation is necessary for the normal functioning of the heart. Presently there are three major characteristics of proper electrical activation of a heart: (1) left ventricle (LV) activation before RV activation, (2) in the LV, endocardial activation before epicardial activation, and (3) in both the RV and LV, apex activation before base activation. The earliest electrical activation typically occurs at the endocardium of the lower left side of the septum and the lower anterior wall.

Recent experiments have shown that creation of an activation sequence similar to that of the natural contraction of the heart contributed to better heart functioning. Patients with poor atrio-ventricular conduction (AV-block) or poor sinus-node function typically receive a ventricular pacemaker. Such pacemakers restores the normal heart operation. However, the traditional position of the ventricular lead is the right ventricular apex. This pacing location may not provide optimal heart functioning and may result in ventricular remodeling.

Further, use of ventricular pacing is to resynchronize the ventricular activation. This is mainly used in patients with heart failure (HF) who also have left bundle branch block (LBBB). LBBB causes a sequence of activation similar to that during RV apex pacing. In the LBBB patients, left ventricular (LV) or biventricular pacing (BiV) is used to resynchronize ventricular activation, with good results.

Although LV pacing sites may offer great advantages over RV pacing sites, positioning of the leads is cumbersome. For example, thoracotomy is used to position a lead at the LV wall, but this invasive procedure does not offer significant advantages over the transvenous approach. In the transvenous approach, LV pacing leads are positioned in coronary veins, which can be difficult, time consuming, and not reliable because of lead displacement. Moreover, even if the lead can be positioned in a coronary vein, individual heart anatomies differ widely, such that the preferred site could be difficult to locate for lead replacement.

Recently a trans-atrial septal approach was introduced to enable LV endocardial pacing. In this approach the pacing lead is advanced from the right atrium through the right atrial septum wall into the left atrium and through the mitral valve into the LV cavity until a proper site at the LV endocardium is reached. A disadvantage with this approach is that a large part of the lead is permanently inside of the LV cavity. One of the many clinical concerns with the trans-atrial septal approach is Emboli originating from this lead may enter the systemic circulation giving rise to strokes.

BRIEF SUMMARY OF THE INVENTION

A lead system includes attachment means into the trans-ventricular system to attach to a location in the LV. The lead system is introduced from the RV side and enables a more reliable site selection in the LV and provides a secure semi-exogenous lead attachment to the LV.

DRAWINGS

FIG. 5 shows a trans-septal pacing approach using a pacing lead in an embodiment of the present teachings;

FIG. 6 shows a trans-myocardial pacing approach using a pacing lead in an embodiment of the present teachings;

FIG. 11 shows a side profile of a pacing lead in an embodiment of the present teachings;

FIG. 12 shows a distal end profile of the pacing lead of FIG. 11 in a unipolar embodiment of the present teachings;

FIG. 13 shows a distal end profile of the pacing lead of FIG. 11 in a bipolar embodiment of the present teachings;

FIG. 14 shows a pacing lead during insertion in an embodiment of the present teachings;

FIG. 15 shows a pacing lead after insertion in an embodiment of the present teachings;

FIG. 17 shows a pacing lead during insertion in an embodiment of the present teachings;

FIG. 18 shows a pacing lead after insertion in an embodiment of the present teachings;

DESCRIPTION OF VARIOUS EMBODIMENTS

Figure 1:
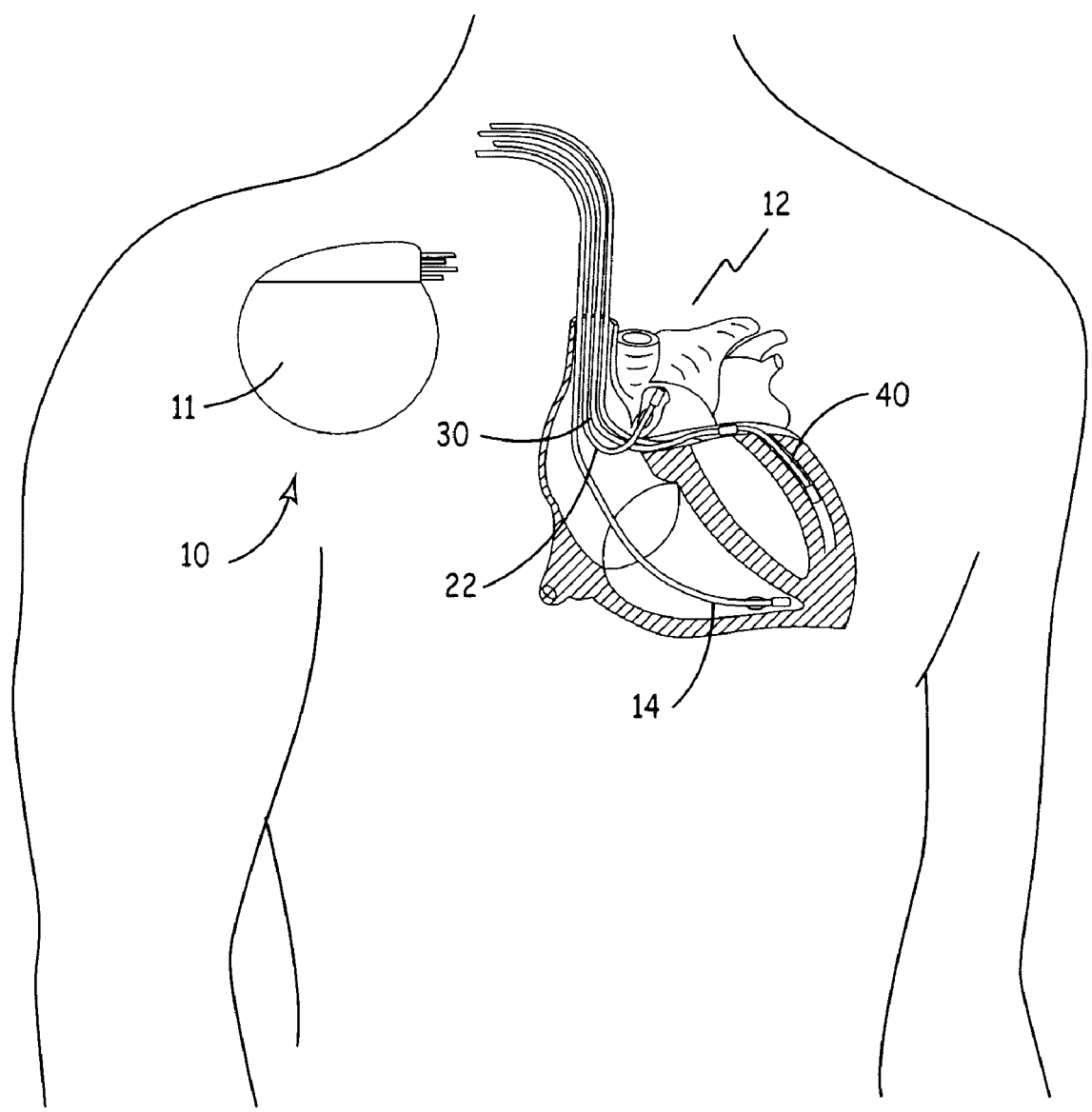
FIG. 1 shows a schematic view of the general environment of implantable medical device ("IMD")

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

With respect to FIG. 1, a schematic view of the general environment of implantable medical device ("IMD") is shown. IMD 10 shown in FIG. 1 is a pacemaker comprising at least one of pacing and sensing leads 14, 22, 30, and 40 attached to hermetically sealed enclosure 11 and implanted near human or mammalian heart 12. Pacing and sensing leads 14, 22, 30, and 40 sense electrical signals attendant to the depolarization and re-polarization of heart 12, and further provide pacing pulses for causing depolarization of cardiac tissue in the vicinity of the distal ends thereof. Leads 14, 22, 30, and 40 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
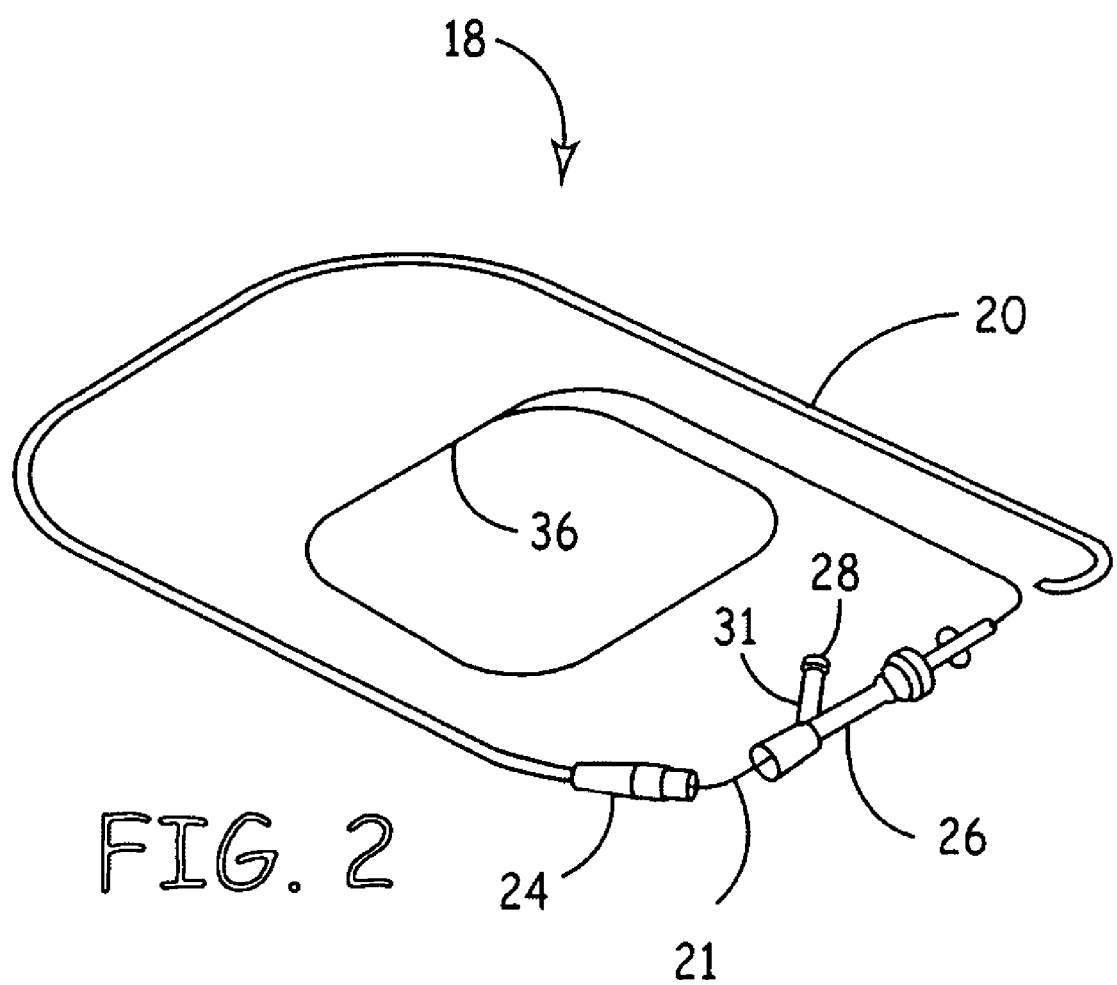
FIG. 2 shows a right perspective view of an embodiment of the pacing lead assembly for the present teachings.

With reference to FIG. 2, a right perspective view of an embodiment of a lead assembly utilizing catheter insertion is shown. Lead assembly 18 comprises guide catheter 20 and lead body 21. Lead body 21 is received by and fits slidingly within guide catheter 20. Hub 24 is located at the proximal end of guide catheter 20. Hemostasis valve 26 may be attached to the proximal end of hub 24. Removal of sealing cap 28 from neck 31 permits the introduction of saline solution, anticoagulants, and intravenously administered drugs through valve 26. The proximal end of valve 26 receives lead body 21 and guides it through hub 24 into guide catheter 20.

Figure 3:
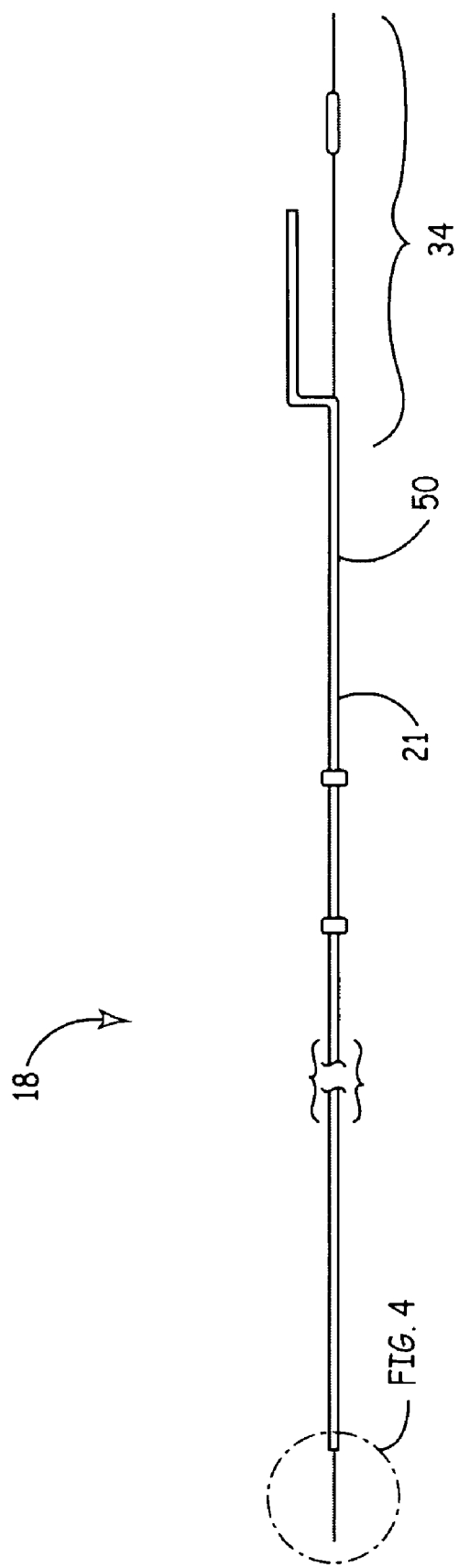
FIG. 3 shows a side view of an embodiment of a lead body in an embodiment of the present teachings.

With reference to FIG. 3, a side view of the lead body in an embodiment of an implantable lead body for the present teachings is shown. Lead body 21 has a proximal end 34 with a connector 54 (FIG. 4) for establishing electrical connection between lead assembly 18, an IMD 10, and the tissue of heart 12. Electrically insulative outer sheath 50 is formed of biocompatible material such as a suitable polyurethane or silastic compound, and protects electrical conductor 54 disposed within lead body 21 from the corrosive effects presented by body fluids. Sheath 50 additionally prevents conductor 54 disposed within lead body 21 from shorting to the body. It is fully contemplated there can be more than one connector, as is discussed below, without departing from the spirit of the teachings.

Figure 4:
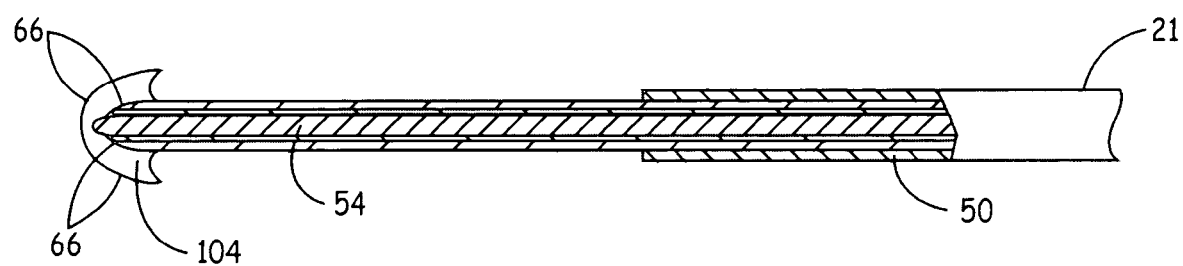
FIG. 4 shows an enlarged axial cross-sectional view of a distal end of a lead body in an embodiment of the present teachings.

With reference to FIG. 4, an enlarged axial cross-sectional view of lead body distal end in an embodiment of the present teachings is shown. Conductor 54 can be three strands of left-hand-wound twisted MP35-N wire, and can be capable of reliably conducting electrical current after having been subjected to numerous, repeated bending and torquing stresses. However, conductor 54 may comprise a single wire formed of a nickel-titanium alloy such as nitinol. Lead body 21 has a diameter of about 3 French in some embodiments, but may have a diameter as great as about 4 French or as small as about 2 French. Conductor 54 is mechanically and electrically connected to electrode 66. Conductor 54 and electrode 66 can be connected by laser welding however other methods of connection are contemplated. Operably coupled to electrode 66 is an occlusion fabric 104. Occlusion fabric 104 can be made of most any type of material as long as the material can be implanted within the body. For example, occlusion fabric 104 could be made of Dacron. Further, occlusion fabric 104 could be attached to electrode 66 in a plurality of ways, such as stitching fabric 104 to electrode 66 or fabric 104 could have pockets to receive the electrode 66. Regardless of how electrode 66 is coupled to fabric 104, it is beneficial for portions of the surface of electrode 66 to be exposed to provide good electrical conductivity to heart 12.

With reference to FIG. 5, a trans-septal pacing approach using a pacing lead in an embodiment of the present teachings is shown. The present teaching discloses positioning a pacing lead in heart 12 at septum 100 or at myocardial wall 102. In a trans-septal pacing approach, a standard transvenous entrance is used to advance lead 18 towards ventricular septum 100. The same transvenous entrance would be used to advance a pacing lead 19 to the base of right ventricle 106 to pace the right ventricle as is know in the art. From there lead 18 penetrates ventricular septum 100 until the lead protrudes into the LV cavity. Then lead 18 is withdrawn, until electrode 66 is against the left septal endocardium 100 and occlusion fabric 104 operably coupled to electrode 66 rests against the left septal endocardium blocking the hole created during penetration of ventricular septum 100 by lead 18. This arrangement places the lead in an embedded position in the transventricular system, which enables sensing, detection, and pacing in the LV. As mentioned above, the lower part of the LV septum is substantially the general location where activation starts in the normal heartbeat. With trans-septal pacing the electrical impulse will presumably spread from the septal apex to the base, from endocardium to epicardium and cause the LV side of the septum to be activated before the RV. Therefore, trans-septal pacing combines a relatively easy implantation procedure with minimal risk for formation of emboli and with a sequence of activation similar to the normal activation pattern. The latter will result in optimal LV ejection fraction and minimized remodeling as compared to RV apex pacing.

With reference to FIG. 6, a trans-myocardial pacing approach using a pacing lead in an embodiment of the present teachings is shown. In a trans-myocardial pacing approach, a standard surgical procedure is used to advance lead 18 towards ventricular myocardial wall 102. From there lead 18 penetrates ventricular wall 102 until the lead enters the LV cavity. Then lead 18 is withdrawn, until electrode 66 is against the left septal endocardium and an occlusion fabric 104 operably coupled to electrode 66 rests against the left septal endocardium blocking the puncture created during penetration of the ventricular septum by lead 18.

Figure 7:
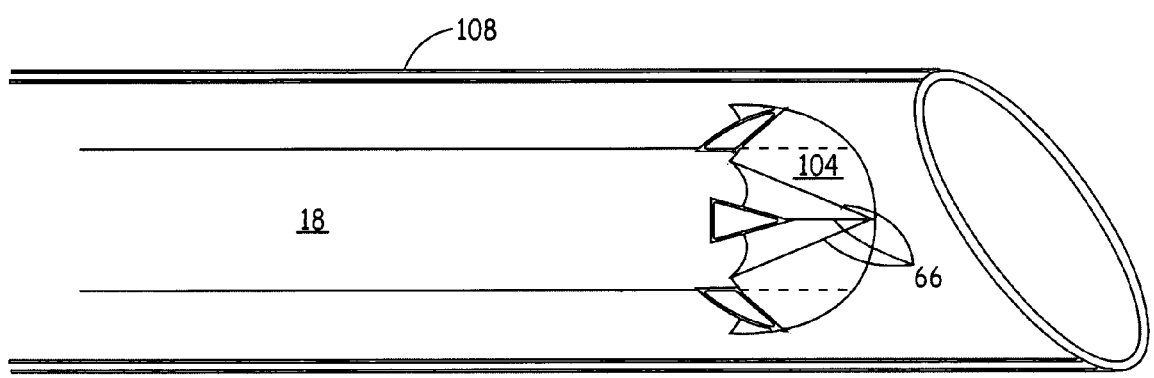
FIG. 7 shows a heart wall penetration system for delivery of a pacing lead in an embodiment of the present teachings.

With reference to FIG. 7, a heart wall penetration system for delivery of a pacing lead in an embodiment of the present teachings is shown. Penetration of septum 100 or heart wall 102 could be accomplished in a plurality of ways; however, for the purpose of the disclosure penetration will be discussed with respect to a catheter. A stiff, curved guide catheter 108 can be positioned into right ventricle 106 or close to ventricular wall 102. Through catheter 108 a force can be applied to penetrate ventricular septum 100 or ventricular wall 102. As discussed above, however, penetration of septum 100 or heart wall 102 can be accomplished in a plurality of ways such as by advancing a sharp steel wire, thus creating a hole, then withdrawing the wire and introducing the pacing lead through the hole, with a pacing lead having a sharp tip, or by placing a stiffening stylet in a pacing lead that makes the lead stiff enough to penetrate the heart wall.

Pacing the right ventricle maintains normal ventricular activation in case of AV-block or sick sinus syndrome. In these patients cardiac function can be better maintained and remodeling of the heart is likely prevented or reduced. Moreover, since the right ventricular pacing site is likely distal to the block in the case of Left Branch Bundle Block (LBBB), right ventricle pacing may also be used for resynchronization therapy in heart failure LBBB pacing, instead of the coronary venous approach.

Figure 8:
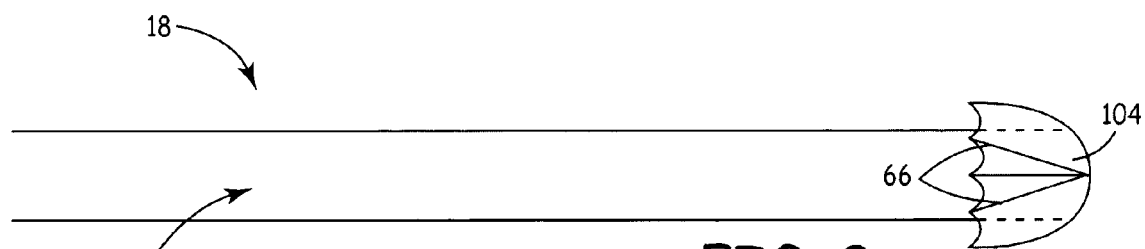
FIG. 8 shows a side profile of a pacing lead in an embodiment of the present teachings.
Figure 9:
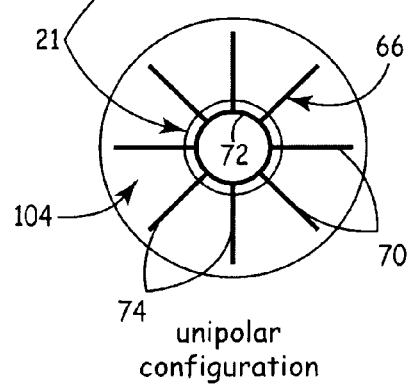
FIG. 9 shows a distal end profile of the pacing lead of FIG. 8 in a unipolar embodiment of the present teachings.
Figure 10:
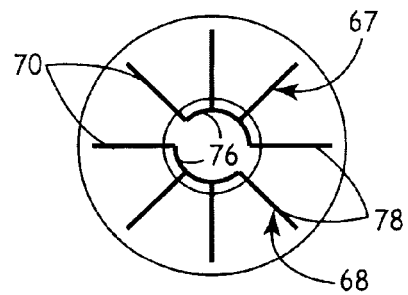
FIG. 10 shows a distal end profile of the pacing lead of FIG. 8 in a bipolar embodiment of the present teachings.

With reference to FIG. 8, a side profile of a pacing lead in an embodiment of the present teachings is shown. As discussed above, lead 18 comprises lead body 21, conductor 54, electrode 66, and occlusion fabric 104. In FIG. 9, electrode 66 provides a cambered fabric support 70 comprising a center portion 72 and legs 74, which extend out from center portion 72 in a cambered fashion. This cambered form allows occlusion fabric 104 to take the shape of an collapsible canopy, which assists in occluding the puncture in the heart wall created by catheter 108. It's helpful if electrode 66 is made of a flexible, strong, and electrically conductive material such as MP35N. This allows legs 74 to be compressed against body 21 when inside of the insertion catheter 108, expand to its cambered form upon exiting catheter 108, and expand further outward when electrode 66 is pulled back towards the left ventricular wall as will be discussed in more detail below. FIG. 9 shows a unipolar configuration where electrode 66 has a single polarity. FIG. 10 shows a bipolar lead configuration where electrodes 67 and 68 have opposite polarities or one of the two is used to sense electrical activity. Electrode 67 and 68 still provide a cambered fabric support 70 comprising a center portion 76 and legs 78.

With reference to FIG. 11, a side profile of a pacing lead in an embodiment of the present teachings is shown. In FIG. 12, electrode 80 provides a cambered fabric support 82 comprising a center portion 84 and legs 86, which extend out from center portion 84 in a cambered fashion. In this embodiment, occlusion fabric 104 has a leaflet shape. FIG. 12 shows a unipolar configuration where electrode 80 has a single polarity. FIG. 13 shows a bipolar lead configuration where electrodes 88 and 90 have opposite polarities or one of the two is used to sense electrical activity. Electrode 88 and 90 still provide a cambered fabric support 82 comprising a center portion 92 and legs 94.

Figure 16:
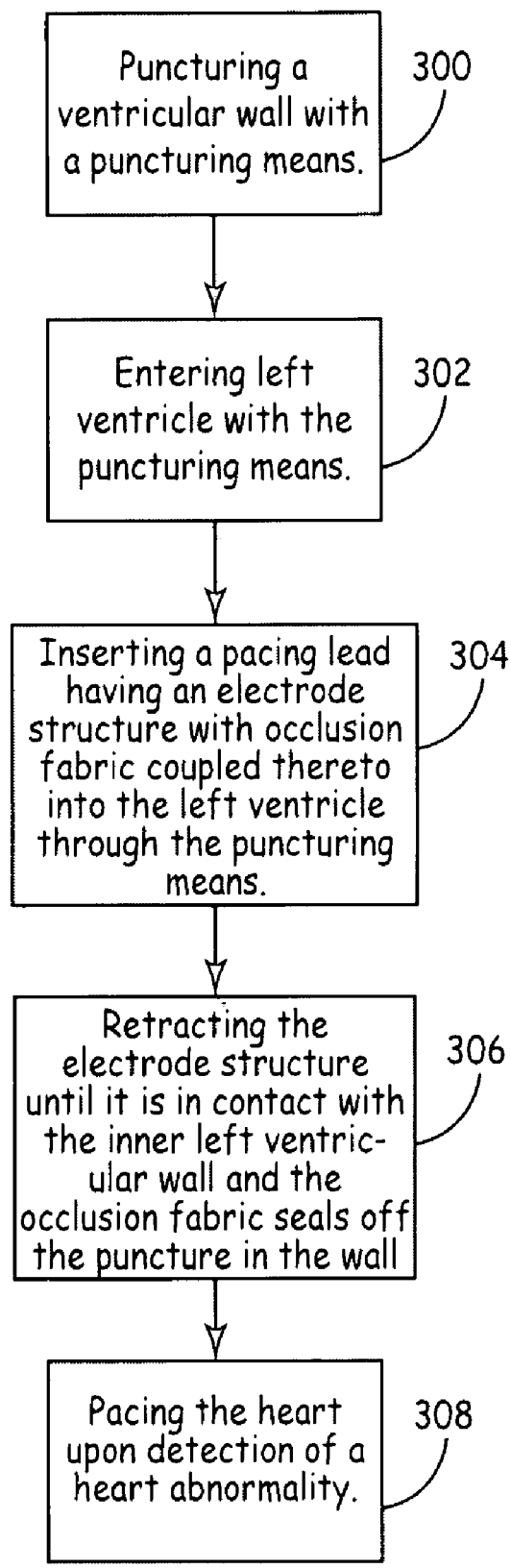
FIG. 16 shows a flowchart diagram of a method for pacing a heart in an embodiment of the present teachings.

With reference to FIGS. 14-16, a pacing lead during insertion and implantation as well as a method for pacing in an embodiment of the present teachings is shown. As discussed above, during insertion catheter 108 is used to create a hole 200 through ventricular walls 100 or 102 (step 300). Once catheter 108 reaches the left ventricle 107 (step 302) the clinician would push lead 18 through catheter 108 into left ventricle 107 (step 304) and remove catheter 108. Cambered support structure 70 then expands in an collapsible canopy shape. Lead 18 can then be retracted (step 306) so that cambered support structure 70 further expands as shown in FIG. 15 to seal off hole 200. This retraction action also causes electrode 66 or 67 and 68 to be pressed against inner portion 210 of ventricular wall 100 or 102. Over time scar tissue would grow over occlusion fabric 104 thus assisting in holding fabric 104 over hole 200. Additionally, tines 202, which are covered by fabric 104 during insertion, pop out when the collapsible canopy unfolds and allow the clinician to retract lead 18 to back electrode 66 against inner wall 100 or 102, but prevent the clinician from pushing the electrode back into the ventricle again thus anchoring lead 18. It is further contemplated tines 202 could be connected to a conductor to act as an electrode thus providing bipolar pacing. After lead 18 is implanted pacemaker 10 could then detect any heart abnormalities and provide a pacing therapy if necessary (state 308).

With reference to FIGS. 17 and 18, a pacing lead during insertion and implantation in an embodiment of the present teachings is shown. Lead 18 is formed with a serrated edge 212 to provide another anchoring structure. After insertion of catheter 108 and retraction of lead 18 causing electrode 66 or 67 and 68 to be pressed against inner portion 210 of ventricular wall 100 or 102, a fixation ring 220/222 can be slid down over lead 18 to serrated edge 212. Fixation ring 220/222 is then slid over serrated edge 212 until it abuts right ventricle wall 230. Fixation rings 220/222 can be pushed towards the distal end of lead 18; however, serrated edge 212 prevents fixation rings 220/222 from being pulled back towards the proximal end of lead 18. Therefore, fixation rings 220/222 is combination with serrated edge 212 act similar to a tie strap in that fixation rings 220/222 lock in place to prevent lead 18 from being pushed into left ventricle 107. Over time scar tissue would grow over occlusion fabric 104 thus assisting in holding fabric 104 over hole 200. Additionally, fixation ring 222 has eyelets 224 which allow for a clinician to suture fixation ring to heart 12 when using a trans-myocardial implantation approach.

Figure 19:
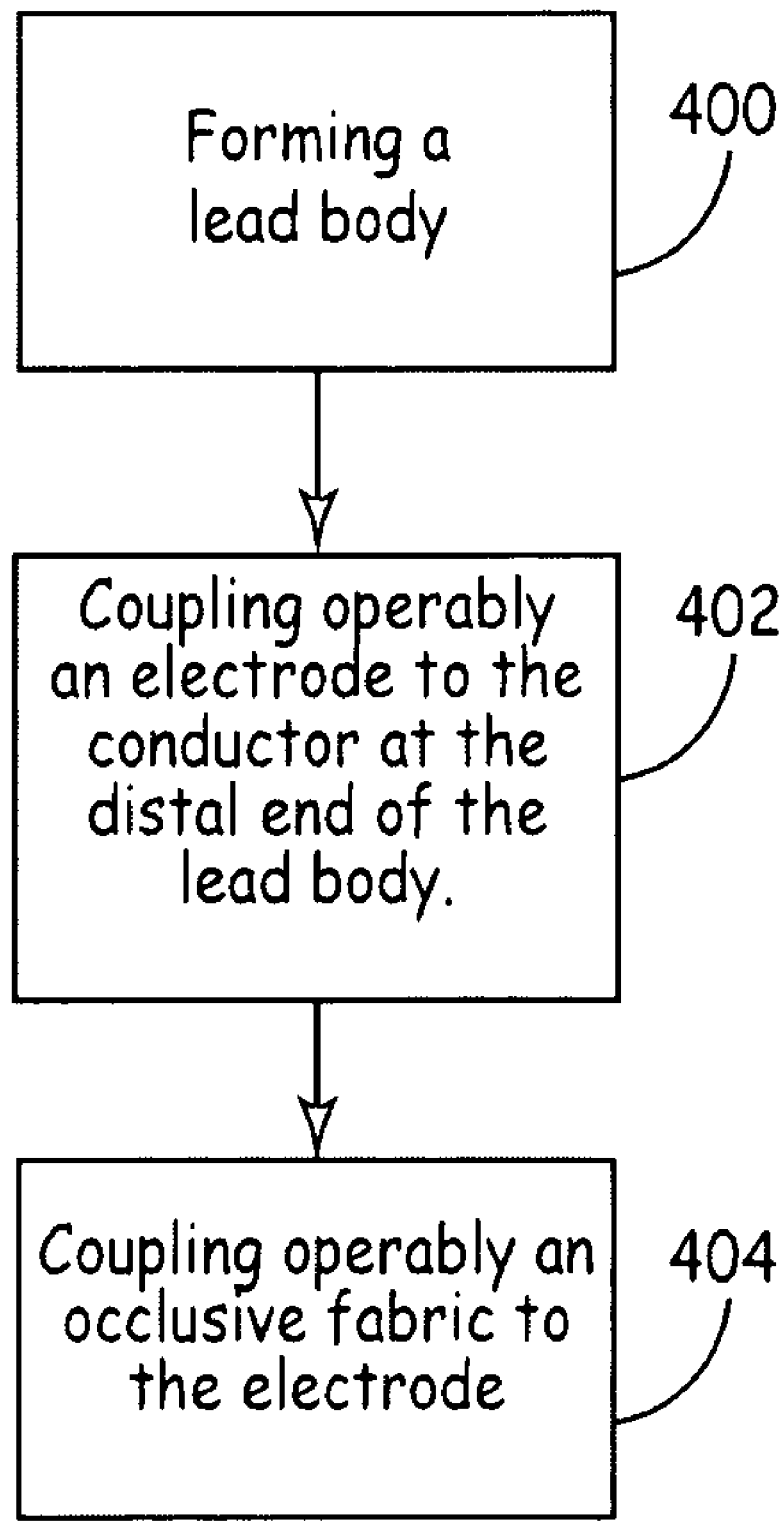
FIG. 19 shows a flowchart diagram of a method of manufacturing a pacing lead in an embodiment of the present teachings.

With reference to FIG. 19, a flowchart diagram of a method of manufacturing a pacing lead in an embodiment of the present teachings is shown. As discussed above, lead 18 can have a lead body 21 formed of an electrically insulative outer sheath 50 of biocompatible material such as a suitable polyurethane or silastic compound (step 400). Lead body 21 protects electrical conductor 54 disposed within lead body 21 from the corrosive effects presented by body fluids. Conductor 54 is mechanically and electrically connected to electrode 66 (step 402). Operably coupled to electrode 66 is an occlusion fabric 104 (step 404). Occlusion fabric 104 could be attached to electrode 66 in a plurality of ways, such as stitching fabric 104 to electrode 66 or fabric 104 could have pockets to receive the electrode 66.

Figure 20:
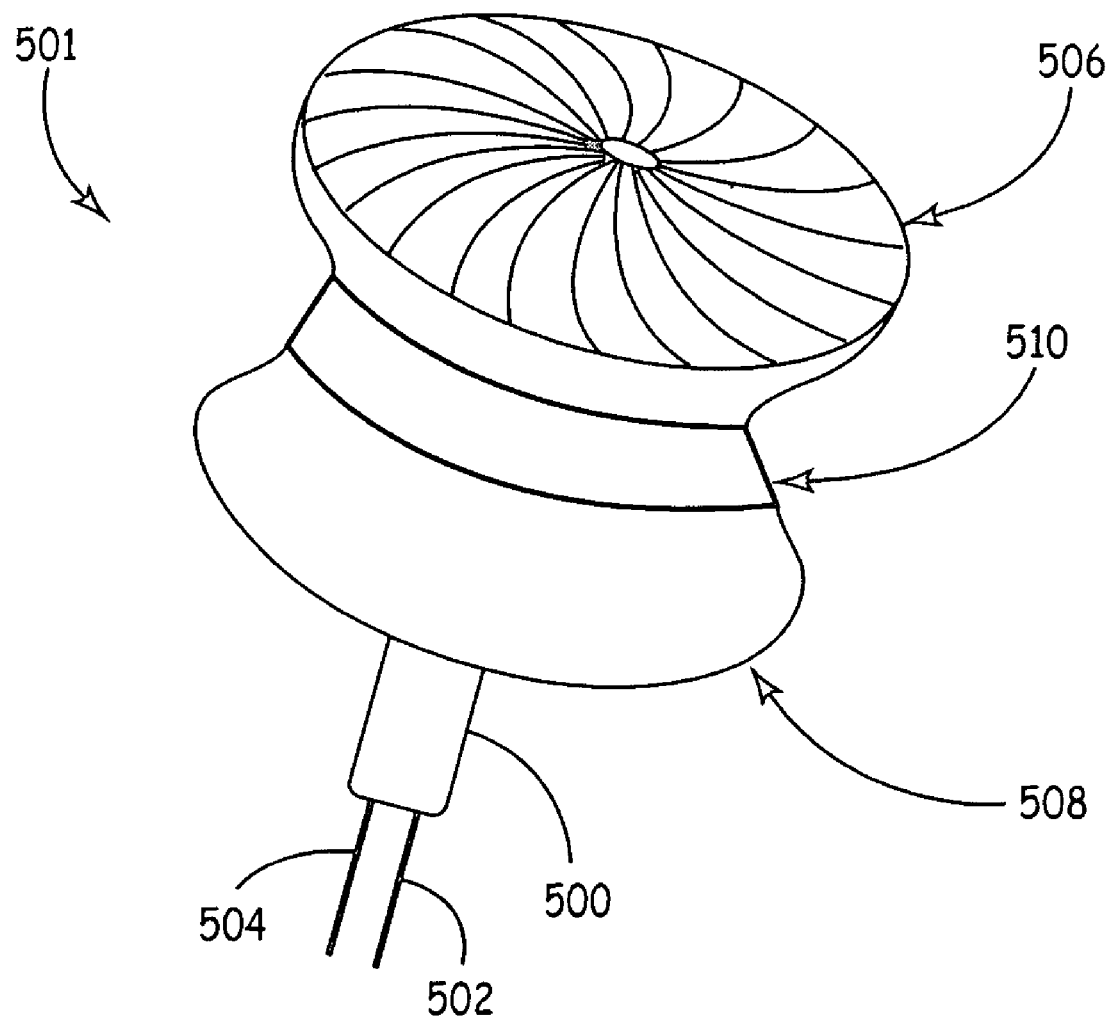
FIG. 20 shows a pacing lead in an embodiment of the present teachings.

With reference to FIG. 20, a pacing lead in an embodiment of the present teachings is shown. Lead body 500 is formed of a biocompatible material such as silicon rubber or polyurethane. Lead body 500 can have electrodes 502 and 504, which can be operably coupled to electrode 506 and 508 respectively. Electrodes 506 and 508 could be formed of a flexible, elastically deformable material such as near-stoichiometric nickel/titanium alloy, commonly referred to as Nitinol or NiTi. Such superelastic materials may be elastically deformed to a much greater extent than most other materials, yet substantially fully recover their original shape when released. This permits electrodes 506 and 508 to be deformed sufficiently for insertion into, and passage through, a small-diameter catheter yet automatically elastically returns to its initial shape upon exiting the catheter. A strip of insulation 510 is placed between electrodes 506 and 508 and acts to electrically separate electrodes 506 and 508, but insulation 510 also acts to occlude hole 200 during implantation of lead 501. Insulation 510 can be made of most any insulative material such as Dacron and, like electrodes 506 and 508, is relatively elastic so it can be compressed when within a catheter and yet fully expand when removed from the catheter during installation.

Thus, embodiments of the Trans-Septal/Trans-myocardial Ventricular Pacing Lead are disclosed. One skilled in the art will appreciate that the present teachings can be practiced with embodiments other than those disclosed. The disclosed embodiments are presented for purposes of illustration and not limitation, and the present teachings are limited only by the claims that follow.

The invention claimed is:

1. A medical electrical lead, comprising:
a lead body having a proximal end and a distal end;
a conductor traversing from the proximal end to the distal end;
an electrode disposed at the distal end of the lead body and electrically coupled to the conductor adapted to electrically stimulate a heart, the electrode extending radially outward from the lead body and being flexible;
occlusion fabric supported by the electrode, the occlusion fabric being flexible, the flexibility permitting the occlusion fabric and the electrode to conform to a surface of the heart to cap punctures in the heart, wherein the electrode provides a cambered fabric support structure for the occlusion fabric, and the occlusion fabric is operably coupled to the cambered fabric support structure and comprises a collapsible canopy; and
a tine that is covered by the cambered fabric support structure during implantation of the medical lead.

2. The lead of claim 1, wherein the tine is exposed after insertion of the distal end into the left ventricle, the tine oriented to allow withdrawal of the distal end from the left ventricle and prevent further movement of the distal end into the left ventricle.

3. The lead of claim 1, wherein the occlusion fabric is operably coupled to the cambered fabric support structure and is in the shape of leaflets.

4. The lead of claim 1, wherein the distal end can be inserted into the left ventricle with a catheter or a trans-septal bore needle.

5. A medical electrical lead, comprising:
a lead body having a proximal end and a distal end;
a conductor traversing from the proximal end to the distal end;
an electrode disposed at the distal end of the lead body and electrically coupled to the conductor adapted to electrically stimulate a heart; and
occlusion fabric disposed at the distal end of the lead body and supported by the electrode in a shape adapted to cover puncture in the heart, wherein the electrode provides a cambered fabric support structure for the occlusion fabric and has a center portion with legs extending outward in a cambered fashion.

6. The lead of claim 5, wherein the occlusion fabric is adapted to cover a portion of the transventricular septum or the myocardial wall.

7. The lead of claim 6, wherein the occlusion fabric is adapted to cover a portion of the ventricular septum or the ventricular myocardial wall.

8. The lead of claim 6, wherein the electrode is adapted to be in electrical contact with the left ventricular side of the transventricular system.

9. The lead of claim 5, further comprising a second electrode adapted to provide bipolar electrical stimulation of the heart.

10. The lead of claim 5, wherein the occlusion fabric is an electrically insulative material.

11. The lead of claim 5, wherein the occlusion fabric operably couples the cambered fabric support structure and comprises a collapsible canopy.

12. The lead of claim 5, wherein the occlusion fabric is operably coupled to the cambered fabric support structure and is in the shape of leaflets.

13. A medical electrical lead, comprising:
a lead body having a proximal end and a distal end;
a conductor traversing from the proximal end to the distal end;
an electrode disposed at the distal end of the lead body and electrically coupled to the conductor adapted to electrically stimulate a heart, the electrode extending radially outward from the lead body and being flexible;
occlusion fabric supported by the electrode, the occlusion fabric being flexible, the flexibility permitting the occlusion fabric and the electrode to conform to a surface of the heart to cap punctures in the heart, wherein the distal end has a saw-tooth shaped surface.

14. The lead of claim 13, further comprising a fixation ring that can be pushed over the saw tooth surface wherein the fixation ring cannot be retracted and the distal end of the lead cannot be pushed further into the left ventricle.

15. The lead of claim 14, wherein the fixation ring has a diameter larger than the diameter of the aperture in the heart.

* * * * *